(12) United States Patent
Farmer et al.

(10) Patent No.: US 9,568,421 B2
(45) Date of Patent: Feb. 14, 2017

(54) GRAPHENE LAYERS FOR IDENTIFICATION OF PRODUCTS

(71) Applicant: International Business Machines Corporation, Armonk, NY (US)

(72) Inventors: Damon B. Farmer, White Plains, NY (US); Dirk Pfeiffer, Croton on Hudson, NY (US); Joshua T. Smith, Croton on Hudson, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/217,064

(22) Filed: Jul. 22, 2016

(65) Prior Publication Data

US 2016/0325580 A1 Nov. 10, 2016

Related U.S. Application Data

(63) Continuation of application No. 14/599,637, filed on Jan. 19, 2015.

(51) Int. Cl.
*G01N 21/00* (2006.01)
*G01N 21/53* (2006.01)
*G01J 1/16* (2006.01)

(52) U.S. Cl.
CPC ............. *G01N 21/534* (2013.01); *G01J 1/16* (2013.01)

(58) Field of Classification Search
CPC .... G01N 21/534; G01N 21/59; G01N 21/255; G01J 3/42; G01J 1/16
USPC ......................................................... 356/434
See application file for complete search history.

(56) References Cited

U.S. PATENT DOCUMENTS

| | | | |
|---|---|---|---|
| 6,869,015 B2 | 3/2005 | Cummings et al. | |
| 7,595,727 B2 | 9/2009 | Grijalva et al. | |
| 8,063,779 B2 | 11/2011 | Coveley et al. | |
| 8,253,536 B2 * | 8/2012 | Kaminska | B42D 25/29 235/491 |
| 9,013,272 B2 * | 4/2015 | Kaminska | B42D 25/29 235/494 |
| 9,390,649 B2 * | 7/2016 | Hack | G09G 3/3208 |
| 2003/0059649 A1 | 3/2003 | Saliba et al. | |
| 2008/0240430 A1 | 10/2008 | Pinchen et al. | |
| 2008/0276817 A1 | 11/2008 | Hinch et al. | |

(Continued)

OTHER PUBLICATIONS

Bae et al., "Roll-to-roll production of 30-inch graphene films for transparent electrodes", Nature Nanotechnology, Aug. 2010 (online Jun. 2010), vol. 5, pp. 574-578, © 2010 Macmillan Publishers Limited. DOI: 10.1038/NNANO.2010.132.

(Continued)

*Primary Examiner* — Tarifur Chowdhury
*Assistant Examiner* — Md A Rahman
(74) *Attorney, Agent, or Firm* — Nolan M. Lawrence

(57) ABSTRACT

Aspects of the present disclosure relate to a security device, in particular, a multilayered security device. The multilayered security device includes a substrate layer having a first substrate. The substrate layer attaches to the product. The multilayered security device also includes a graphene layer. The graphene layer has a first continuous graphene sheet that is made of a monolayer of covalently-bonded carbon atoms. The graphene layer also forms, in response to exposure to a verification stimulus, a contrasting pattern with respect to an exposed substrate area from the substrate layer.

9 Claims, 13 Drawing Sheets

(56) References Cited

U.S. PATENT DOCUMENTS

| | | |
|---|---|---|
| 2010/0050901 A1 | 3/2010 | Biris et al. |
| 2011/0076467 A1 | 3/2011 | Huang et al. |
| 2012/0318334 A1 | 12/2012 | Bedell et al. |
| 2013/0008087 A1 | 1/2013 | Paavilainen et al. |
| 2013/0087620 A1 | 4/2013 | Sharma et al. |
| 2014/0050903 A1 | 2/2014 | Lettow et al. |
| 2014/0070082 A1 | 3/2014 | Guo et al. |
| 2014/0087191 A1 | 3/2014 | Chua et al. |
| 2014/0145426 A1 | 5/2014 | Lettow et al. |
| 2015/0129280 A1 | 5/2015 | Lee et al. |
| 2016/0207345 A1 | 7/2016 | Farmer et al. |

OTHER PUBLICATIONS

Blake et al., "Making graphene visible", Applied Physics Letters 91, 063124 (2007), pp. 1-3, © 2007 American Institute of Physics.

Chen et al., "High-quality and efficient transfer of large-area graphene films onto different substrates", an accepted manuscript, Carbon (2013). 19 pages. DOI: http://dx.doi.org/10.1016/j.carbon.2013.01.011.

Chen et al., "The selective transfer of patterned graphene", Scientific Reports, Nov. 2013, 3:3216, pp. 1-6. DOI: 10.1038/srep03216.

Gupta et al., "A facile process for soak-and-peel delamination of CVD graphene from substrates using water", Scientific Reports, 4:3882, pp. 1-6, Jan. 24, 2014 (Recevied Oct. 15, 2013). DOI: 10.1038/srep03882.

Han et al., "Extremely efficient flexible organic light-emitting diodes with modified graphene anode", Nature Photonics, vol. 6, Feb. 2012, pp. 105-110, © 2012 Macmillan Publishers Limited. DOI: 10.1038/NPHOTON.2011.318.

Kang et al., "Efficient Transfer of Large-Area Graphene Films onto Rigid Substrates by Hot Pressing", ACS Nano, vol. 6, No. 6, pp. 5360-5365, May 28, 2012 (Received Mar. 19, 2012), © American Chemical Society. DOI: 10.1021/nn301207d.

Kim et al., "Layer-Resolved Graphene Transfer via Engineered Strain Layers", Science, vol. 342, pp. 833-836, Nov. 15, 2013 (Published Online Oct. 31, 2013, Received Jul. 10, 2013). DOI: 10.1126/science.1242988.

Kobayashi et al., "Production of a 100-m-long high-quality graphene transparent conductive film by roll-to-roll chemical vapor deposition and transfer process", Applied Physics Letters 102, 2013, pp. 023112-1-023112-4, © 2013 American Institute of Pysics.

Li et al., "Transfer of Large-Area Graphene Films for High Performance Transparent Conductive Electrodes", Nano Letters, 2009, vol. 9, No. 12, pp. 4359-4363, © 2009 American Chemical Society. DOI: 10.1021/nl902623y.

Pitt, B., "How many megapixels do you need?", Connect: Digital Photography Review, Published Sep. 19, 2013, 22 pages, http://connect.dpreview.com/post/1313669123/.

Smith et al., "Recent Advances in Graphene Devices and Circuits", 39th Annual COMAC Tech Conference, Mar. 31-Apr. 3, 2014, 4 pages.

Wang, X. et al., "Direct Delamination of Graphene for High-Performance Plastic Electronics", Small, Oct. 2014, No. 4, pp. 694-698, © 2013 Wiley-VCH Verlag GmbH & Co. KGaA, Weinheim.

Wang, Y. et al., "Interface Engineering of Layer-by-Layer Stacked Graphene Anodes for High-Performance Organic Solar Cells", Advanced Materials, 2011, pp. 1-5, © 2011 Wiley-VCH Verlag GmbH & Co. KGaA, Weinheim. DOI: 10.1002/adma.201003673.

Xia et al., "Graphine Nanophotonics", IEEE Photonics Journal, vol. 3, No. 2, Apr. 2011, 4 pages, © 2011 IEEE. DOI: 10.1109/JPHOT.2011.2129591.

IBM Proposal in response to DARPA Supply Chain Hardware Integrity for Electronics Defense (Shield), DARPA-BAA-14-16 / DARPA Microsystems Technology Office. Submitted May 30, 2014 by Dr. Kenneth Rodbell and Carl E. Tayor. 32 pages. Grace Period Disclosure.

IBM, List of IBM Patents or Patent Applications Treated as Related, Jul. 21, 2016, 2 pages.

* cited by examiner

GRAPHENE LAYERS FOR IDENTIFICATION OF PRODUCTS

STATEMENT REGARDING PRIOR DISCLOSURES BY THE INVENTOR OR A JOINT INVENTOR

The following disclosure is submitted under 35 U.S.C. 102(b)(I)(A): IBM Proposal in response to DARPA Supply Chain Hardware Integrity for Electronics Defense (SHEILD) DARPA-BAA-14-16/ DARPA Microsystems Technology Office, Kenneth P. Rodbell, Ph.D, May 30, 2014.

Applicants submit that the aforementioned disclosure is not prior art under AIA 35 U.S.C. 102(a)(1) because it is made by someone who obtained the subject matter from the inventor.

BACKGROUND

The present disclosure relates to security devices, and more specifically, to identification of security devices.

Counterfeiting can be an issue in many product marketing settings. Securing the supply chain with respect to consumer products, using for example cost-effective microchips, may be critical. Products can be refurbished or contain materials and ingredients that are not part of the original composition (e.g. pharmaceuticals). Low cost, and optical machine-readable representation of data attached to products allowed barcodes to remain the dominate method of automating the purchase and monitoring of consumer goods when products leave a factory.

SUMMARY

According to embodiments of the present disclosure, a multilayered security device for verification of a product, a method of manufacturing a multilayered security device, and a method of verifying a product using a multilayered security device are provided.

One embodiment is directed toward a multilayered security device for verification of a product. The multilayered security device includes a substrate layer having a first substrate. The substrate layer attaches to the product. The multilayered security device also includes a graphene layer. The graphene layer has a first continuous graphene sheet that is made of a monolayer of covalently-bonded carbon atoms. The graphene layer also forms, in response to exposure to a verification stimulus, a contrasting pattern with respect to an exposed substrate area from the substrate layer.

Another embodiment is directed toward a method of manufacturing a multilayered security device. The method includes creating a substrate layer. The method also includes transferring one or more layers of graphene sheet onto the substrate layer such that each graphene sheet forms an exposed substrate area on the substrate layer. Each graphene sheet also forms a different contrasting pattern with the exposed substrate area when exposed to a verification stimulus. Each graphene sheet is also created by a process that creates a monolayer of covalently-bonded carbon atoms in a continuous sheet. The method also includes applying a protective coat to the one or more layers of graphene sheet. The method also includes removing a portion of the substrate layer.

Another embodiment is directed toward a method of verifying a product using a multilayered security device. The method includes applying a visible light verification stimulus to a graphene-based security device attached to the product, the graphene-based security device having a substrate layer, one or more graphene sheets that are each made of a monolayer of covalently-bonded carbon atoms. The method also includes receiving a captured pattern from the security device through a capture device. The captured pattern is a result of interaction of the visible light verification stimulus between one or more graphene sheets and a substrate. The method also includes determining whether the captured pattern matches an expected pattern. The method also includes labeling the product as authentic in response to the captured pattern matching the expected pattern.

The above summary is not intended to describe each illustrated embodiment or every implementation of the present disclosure.

BRIEF DESCRIPTION OF THE SEVERAL VIEWS OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
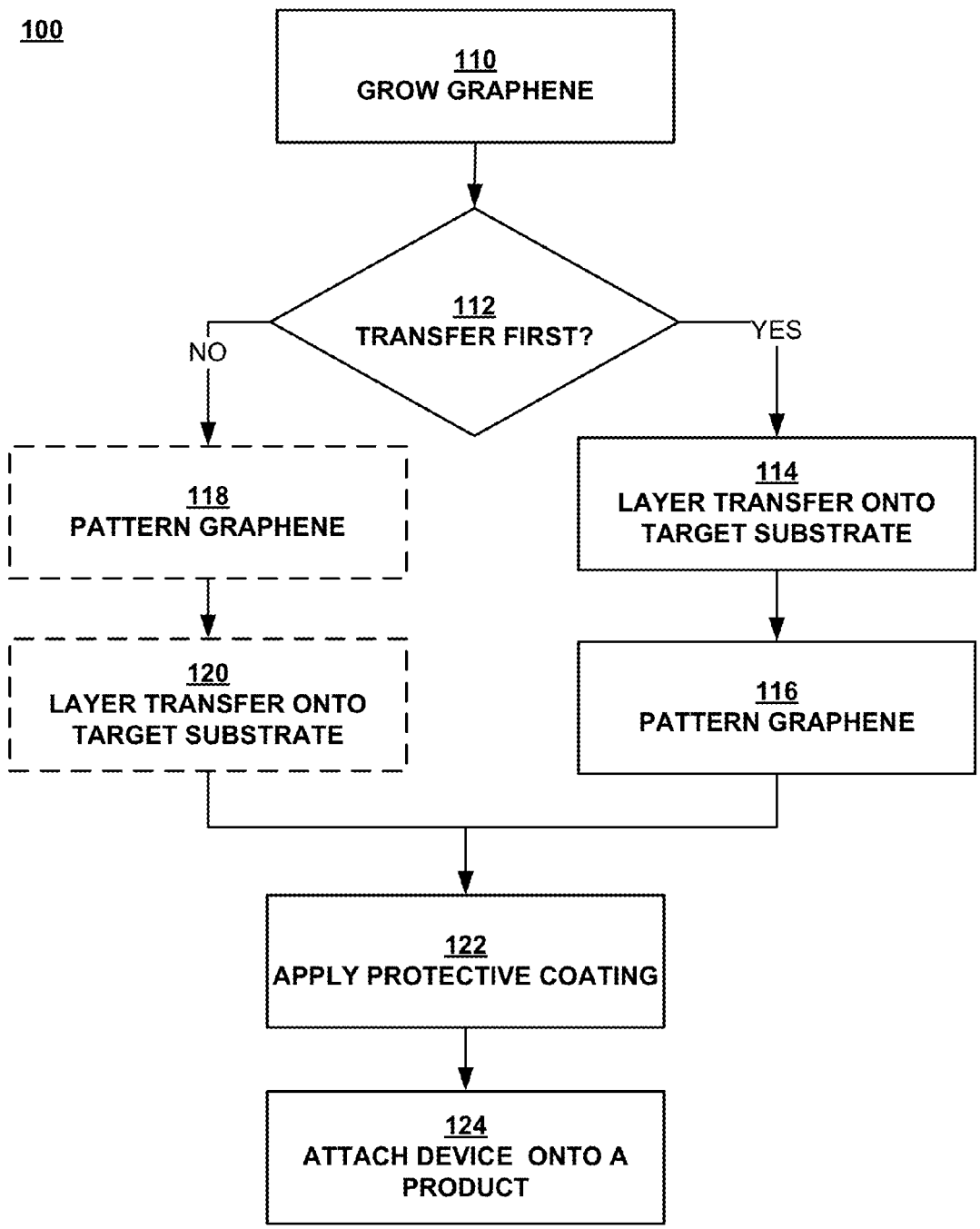
FIG. 1 illustrates a flowchart of a method for making a multilayered security device, according to various embodiments.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present disclosure relates to security devices, and more specifically, to identification of security devices. For instance, aspects of the present disclosure relate to creating a security device with multiple layers. The security device includes at least one graphene layer to create a contrasting pattern with a substrate layer. The contrasting pattern of the security device may be captured using a variety of techniques with a capture device (e.g., a low- or high-resolution camera) and compared to an expected pattern to verify authenticity. While the present disclosure is not necessarily limited to such applications, various aspects of the disclosure may be appreciated through a discussion of various examples using this context.

Barcodes are relatively universal in product identification. Unfortunately, a barcode can be easily removed or copied and then attached to fake or counterfeit products. A security device that features a label that contains a bar code which may be difficult to copy, or removed but is easily identifiable via mobile devices like a cell phone or a handheld scanning device would be highly desirable. A difficult to copy, tamper-proof barcode attached to a genuine product would allow a consumer to authenticate the product by taking a picture of the label using a cell phone camera. After, the captured data representation of the product can be sent to a secure service for authentication.

Aspects of the present disclosure describe the creation of a graphene-based, tamper-resistant barcode or label that can be mass-produced and attached, at the point of origin of manufacture, to the product. After attachment, the label can be read by a hand-held device, e.g., a cell phone, or hand scanner. The tensile properties of graphene may deter the copying, removal, cloning and tampering of the barcode without damage to the graphene layer.

Additionally, a unique fingerprint or barcode may be fabricated into a sheet of graphene using Chemical Vapor Deposition (CVD) growth, layer transfer of the material onto a target substrate, and standard patterning processes. After processing, a multilayered security device (i.e., tag) is produced containing the unique graphene fingerprint which can be glued onto any product for authentication. The fingerprint is formed from a contrasting pattern formed between the substrate and the graphene when a verification stimulus is applied. The fingerprint may be unique to each multilayered security device or batches of multilayered security devices created within the same specifications. Embodiments of the present disclosure allow for using various thermal, or electrical properties of the graphene for identification of a fingerprint. For the purposes of illustration, examples are used that assume that a light source is the verification stimulus and a camera is the capture device.

Graphene has optical, electrical, and thermal properties. Due to optical properties of graphene coupled with the index of refraction of the substrate(s) of the multilayered security device, the graphene patterns can be made visible in the visible light spectrum, allowing the unique barcode to be photographed by a low-resolution digital camera, according to various embodiments. The picture can then be sent via cell phone to a secure server for authentication. Low-resolution digital cameras can be defined by the megapixels. Low-resolution digital cameras are typically under 10 megapixels while high-resolution digital cameras may be over 10 megapixels. Aspects of the present disclosure apply to both low-resolution and high-resolution cameras. Since a graphene layer is only a monolayer in thickness, the graphene layer is very fragile to removal and may be difficult to copy; hence, the tag provides a tamper resistant element. If the item is tagged at its point of origin and is legitimate, the item may resist being cloned or copied downstream.

FIG. 1 illustrates a flowchart of a method 100 for making a multilayered security device, according to various embodiments. The method 100 may involve first growing a graphene layer and transferring the graphene layer to a substrate layer. The graphene layer may be patterned and a protective coating layer may be applied to the graphene. The method 100 may begin at operation 110.

In operation 110, graphene can be grown using a variety of techniques that result in a continuous graphene sheet that is distinguishable from powdered graphene. In various embodiments, electroactive polyimide (EPI) can be used to create a graphene sheet on a Silicon Carbide (SiC) substrate. For example, SiC can be enhanced with an EPI buffer. The EPI buffer can further form a weak bond with the graphene sheet for deposition. In various embodiments, graphene is epitaxially grown on the Silicon face of SiC.

According to various embodiments, the graphene can also be deposited onto an initial substrate using either continuous or island growth CVD. The initial substrate can be a metal, e.g., copper foil, nickel, platinum of various thicknesses (e.g., around 25 μm -36 μm thick copper). The CVD growth can be roll-to-roll processed, where graphene is deposited onto a roll of initial substrate at a particular rate. In various embodiments, the CVD can occur in a high temperature environment, e.g., 1000 Celsius, synthesis. Varying pressures can be used for CVD. Hydrogen or methane gas may also be used to facilitate the deposition. The CVD may also deposit more than one layer of graphene, e.g., 1-10 layers, onto a silicon wafer containing a specific oxide thickness. In various embodiments, the graphene layer may have 1-5 layers of graphene sheets depending on the properties desired of a graphene pattern.

In operation 112, whether a transfer to a substrate occurs first may be determined. In various embodiments, a manufacturer of a graphene security device may determine whether to transfer a layer to the substrate first or pattern the graphene before layer transfer onto the substrate. If the transfer of the graphene layer occurs first, then the method 100 continues to operation 114. The transfer first presents an advantage where the graphene avoids contamination and damage. If the transfer of the graphene layer does not occur first, then the method 100 continues to operations 118 thru 120 where the graphene layer is first patterned before transfer.

The transfer operation 120 may present an advantage where misalignment of the patterned graphene onto a target substrate is inevitable. For example, the graphene pattern may be complex and contain patterned regions, some with a suitable refractive index to make the graphene visible. Operations 118 and 120 can represent an alternate path from operation 114 and operation 116. Operation 118 can correspond to operation 116 and operation 120 can correspond to operation 114.

In operation 114, the graphene layer may be transferred onto a target substrate. The transfer onto a target substrate depends on the technique used. For reference, a variety of techniques are provided. Poly (methyl methacrylate) (PMMA) of varying thickness (e.g., 310 nm-9000 nm) or gold may be used to facilitate transfer from an initial substrate to a target substrate. For example, PMMA may be used to spin-coat the graphene on the initial growth substrate and facilitate transferring the graphene to a polyimide tape intermediary or the target substrate after the growth substrate has been etched.

Examples of a target substrate can include a silicon wafer, Silicon Nitride ($Si_3N_4$), polyethylene terephthalate (PET), polyimide tape, various oxides (e.g., $SiO_2$, $TiO_2$, aluminum oxide) sapphire, or quartz. The graphene can be applied to the target substrate of 90-300 nm thick $SiO_2$ coated silicon wafer, or 125 μm-188 μm thick polyethylene terephthalate (PET) substrate The area of graphene prepared using the techniques ranges from 81 $\mu m^2$-315 $cm^2$ of graphene.

In various embodiments, a protective coating can be applied to the bottom of the target substrate (toward the product), .e.g., thin silicon or SiC, which can then be used to adhere the multilayered security device to the product. If a target substrate is thin enough, then graphene patterns can be visible through the target substrate in visible light.

In various embodiments, the target substrate can be an organic light emitting diode (OLED) attached to a power source like a battery or a radio frequency (RF) coil. The light emitted from the organic light emitting diode may be used to backlight the graphene in order to make graphene patterns visible. The graphene can be layer-transferred on Indium Tin Oxide (ITO). The OLED may be tuned to a specific wavelength of light. In order to visualize the graphene patterns, a cell phone can be used to provide power via RF power to activate the OLED and the cell phone camera can be tuned to the specific wavelength of the OLED to capture an image of the graphene fingerprint. The cell phone camera may be configured to detect specific wavelengths in the visible spectrum without modification to hardware. A cell phone may be modified to transmit wireless power via a low-power RF signal such as Wi-Fi™ or Bluetooth®. Various embodiments provide different methods for transferring graphene to the target substrate.

Various embodiments also provide for various thicknesses of substrate to achieve the desired contrast. For example, a single layer of graphene may not be visible for a substrate thickness of 200 nm of $SiO_2$, unless more layers are added. In various embodiments, ten layers of graphene may be the transition from graphene to bulk graphite. The thickness of $SiO_2$ can also vary from 30 nm to 315 nm depending on the wavelength of light used for a monolayer of graphene and the desired contrast level. For example, a wavelength of 400 nm (blue light) may have sufficient contrast at 75 nm $SiO_2$ thickness, but not for 124 nm $SiO_2$ thickness due to the emittance properties of graphene. The thickness for the target substrate may be estimated based on the number of graphene sheets and the wavelength of light. The method of graphene synthesis may have an impact on optical absorption. For example, optical transmittance of PET (100 μm) and Si (60 μm) with three layers of graphene is approximately 85% at 550 nm wavelength of light, while the optical transmittance of graphene made by thermal release tape is 65%.

In various embodiments, the layer transfer of graphene onto a target substrate, i.e., operation 114 or operation 120 may be optional. For example, graphene can be grown epitaxially on SiC, and the graphene does not need to be transferred. In this example, the graphene layer can be patterned directly on a growth substrate where the growth substrate is the target substrate.

In operation 116, the graphene can be patterned. In various embodiments, patterning may refer to patterning the graphene after transferring it to a substrate. A technique for patterning graphene may involve using a spin resist on top of the graphene, patterning the resist using lithography, and then etching the exposed graphene with an $O_2$ plasma etch. The resist may be removed with a solvent bath while the graphene remains fully intact because van der Waals forces hold the graphene tightly to the substrate. The etch can be mild or not mild. For example, a non-mild negative resist (e.g., Hydrogen silsesquioxane (HSQ)) on positive resist (e.g., PMMA) could also etch the exposed graphene.

Another technique of patterning graphene can involve laser patterning. For example, a femtosecond laser (~100 fs, 800 nm, 80 MHz) can fabricate patterns directly into graphene or expose a photoresist above the patterned graphene.

Patterning can also mean layering of the graphene. For example, the layering involves transferring a second sheet of graphene on top of a first already patterned graphene sheet on a substrate and then applying a new pattern to the first and second sheet of graphene together. The layering creates a more complex pattern, containing visible regions of graphene of varying contrast (depending on the number of layers present). For example, patterning two full sheets of stacked graphene would provide one, darker contrast region compared with the rest of the substrate. In various embodiments, the substrate can be a uniform 90 nm or 300 nm of $SiO_2$, which optically reveals graphene.

In various embodiments, a patterned substrate with regions of $SiO_2$ and regions of other materials may be used. The graphene sheet is continuous throughout the entire patterned region lying flush with the underlying $SiO_2$ substrate and will be optically visible only over the $SiO_2$ regions. Continuous may be defined as having an unbroken graphene sheet and not in pulverized. Continuous graphene sheets may offer more tamper evidence than non-continuous graphene sheets. Graphene over certain thicknesses of $SiO_2$ creates an optically readable region of contrast compared to the surrounding areas. Variations in contrast can be introduced to identify unique patterns, e.g. a patterned substrate with wells of arbitrary shape filled with 90 nm $SiO_2$ and alternately patterned graphene sheets that overlap these $SiO_2$ regions on the substrate would generate an even more complex, unique pattern.

A contrasting pattern may also be formed on the surface of graphene via lithography and/or self-assembly of random patterns. The random patterns may be followed by etching and solvent strip to remove a resist. Additionally, patterns can be further enhanced with block copolymers or polymer with nano particles. The contrasting pattern in graphene is ideally large enough (i.e., at least 100 microns) to be resolved via a cell phone-based digital camera or other capture device. In various embodiments, the contrasting pattern is formed between graphene and the substrate. At particular wavelengths of light, the degree of contrast between the graphene and the substrate forms a contrasting pattern. The contrasting pattern between the graphene and substrate creates a fingerprint.

In operation 122, a protective coating may be applied to the graphene on the multilayered security device. The protective coating may cover the graphene. The protective coating may be a polymer used to protect the graphene from damage and make graphene more visible. For example, applying polymer of a particular index of refraction above and below the graphene may enhance or degrade the contrast with the substrate. In various embodiments, the protective coating may be a polymer with a polyacrylate of a specific thickness. The polyacrylate may be cured/crosslinked with the polymer. The protective coating may be tuned with the substrate thickness to make graphene visible in the visible light spectrum. In various embodiments, the protective coating may be PMMA with a thickness of 140 nm. The thickness may vary slightly from the desired thickness (e.g., 140 nm) due to manufacturing process variations or other factors. Consistent with embodiments, the tolerances for the thickness in the protective coating can be set such that optical and electrical properties of the PMMA are consistent with the expected properties. For example, the tolerances can be set according to the resolution of the capture devices such that the thickness variations are immaterial. In certain embodiments, different materials can be used to create protective coatings that are designed to have the same properties as one another. For instance, 140 nm thick PMMA has refractive index of 1.30-1.46. Thus, other protective coatings may have an index of refraction roughly the same as the 140 nm thick PMMA, or if different, the thickness can be adjusted accordingly. The protective coating may be made of a substance that has sufficient binding to the substrate meeting the same brittleness properties of PMMA.

In operation 124, the multilayered security device may be attached onto a product. The substrate of the security device may be affixed to the product via an adhesive or other permanent means. In various embodiments, the substrate can be thinned prior to being attached to the product. A portion of the substrate may be removed during the thinning to allow for a secure attachment to the product. For example, the substrate opposite of the protective coating may be thinned using Xenon Difluoride ($XeF_2$), Tetramethylammonium Hydroxide (TMAH), potassium hydroxide (KOH), reactive ion etching, grinding/polishing, or laser cutting to level out the substrate for easier adhesive application with the product, e.g., a curved surface may require a curved substrate. The portion of the substrate is less than all of the substrate. The removed portion of the substrate may be discarded. In various embodiments, the substrate thickness can be reduced to amplify certain contrasting characteristics of the multi-level security device as discussed herein.

Figure 2:
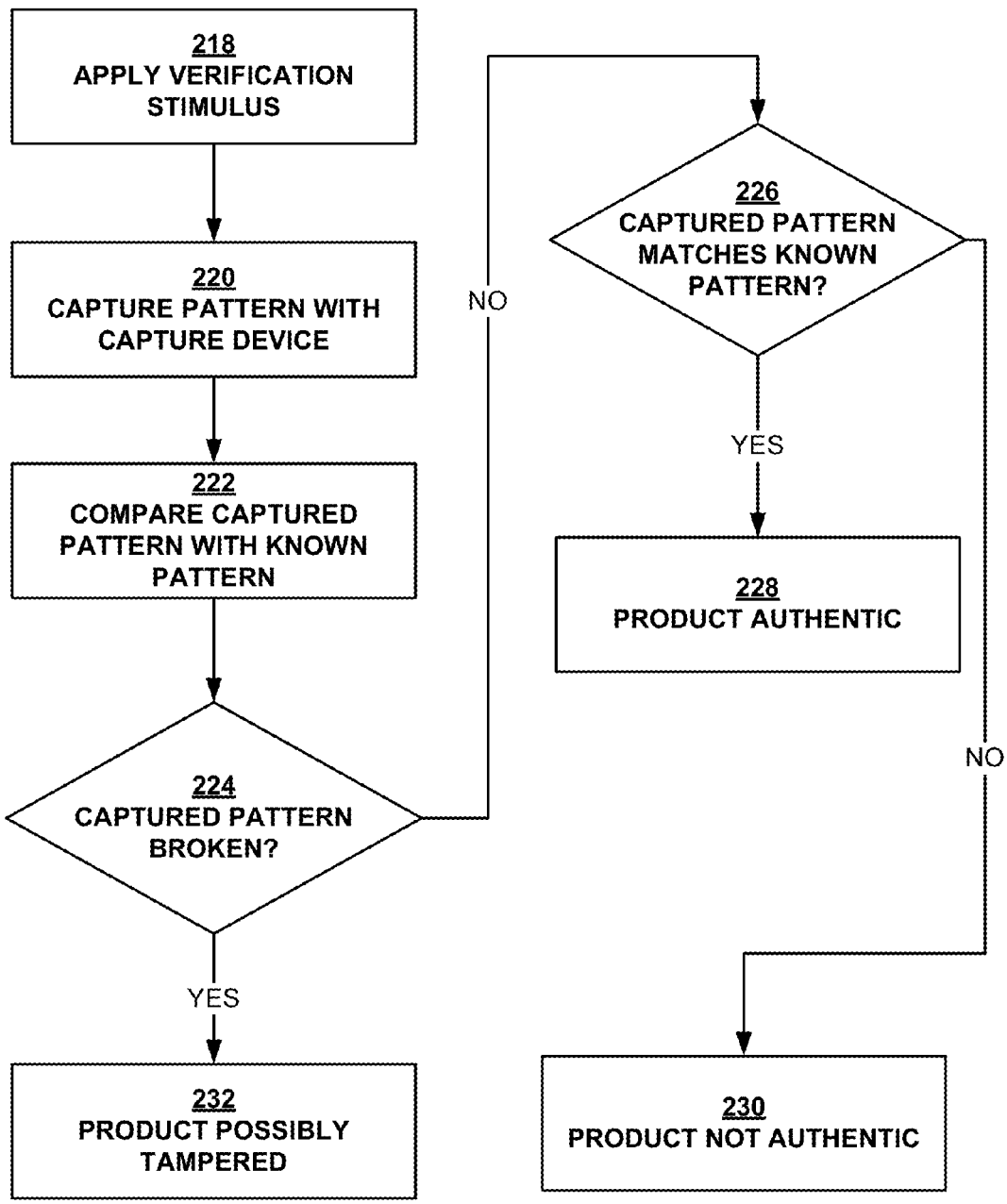
FIG. 2 illustrates a flowchart of a method for verifying the authenticity of the multilayered security device, according to various embodiments.

FIG. 2 illustrates a flowchart of a method 200 for verifying the authenticity of the multilayered security device, according to various embodiments. A product can be verified as authentic by applying a verification stimulus and capturing a pattern with a capture device. In various embodiments, the patterns within the multilayered security device can be indiscernible to a human and would require detection instruments to create a fingerprint for the multilayered security device. For example, the graphene fingerprint may require a high-resolution camera. In which case, a computer analysis system can compare the microscopic differences between a captured pattern and an expected pattern. The method 200 begins at operation 218.

In operation 218, a verification stimulus can be applied to the multilayered security device. The verification stimulus can be a stimulus that is required to produce an action from the multilayered security device. Examples of verification stimulus can include a light source, an electrical charge, radiation, or a thermal source.

The light source may be a multi-wavelength light source (e.g., a light bulb) or can be a single-wavelength, i.e., monochromatic illumination, light source. In various embodiments, filters may be added to the light source to target a particular wavelength of light. Certain wavelengths of light may cause the graphene in the multilayered security device to have a contrast with the underlying substrate. For example, graphene can be isolated on various $SiO_2$ thicknesses for visual detection, For example, at 550 nm of light, a high degree of monolayer graphene contrast may be seen at a sample with 90 nm or 275 nm thickness of $SiO_2$ substrate.

In operation 220, a pattern within the multilayered security device can be captured with a capture device. Assuming a light source verification stimulus, the capture device can be a camera with sufficient resolution to capture the pattern with the graphene. In various embodiments, the camera has at least 1 megapixel (MP) of resolution. In more complex and/or scaled patterns of graphene, higher resolutions, e.g., 10 MP, may be required.

In operation 222, the computer analysis system can compare the captured pattern from operation 220 with the expected pattern or expected pattern as the standard. In various embodiments, the expected pattern can be recorded as numerical properties of various graphene patterns. For example, if there are 0.125 mm spacing between parallel graphene strips, then this can be incorporated into the fingerprint properties. The properties used by the computer analysis system may also be based on a correlation, e.g., in the case of a visual fingerprint, and stored as a comparison image to be compared using computer vision techniques.

In operation 224, the computer analysis system can determine whether the captured pattern is broken. For example, the fragility of a graphene sheet allows for breaking when the multilayered security device is tampered. If the captured pattern is broken, i.e., not continuous, then the computer analysis system can label the product as possibly tampered in operation 232. If the captured pattern is not broken, then the method 200 can continue to operation 226.

In operation 226, the computer analysis system can determine whether the captured pattern matches the expected pattern. To determine whether there is a match, the computer analysis system can use a variety of techniques. For the visual fingerprint example, the computer analysis system can use image processing techniques, e.g., edge detection, thresholding, segmentation, or pattern recognition. In various embodiments, the computer analysis system can give a confidence score to determine how likely the captured pattern matches the expected pattern. If the captured pattern has a threshold met by a confidence score, then the computer analysis system can determine a match and that the product is authentic in operation 228. If there is not a match, then the computer analysis system can determine that the product is not authentic in operation 230. In various embodiments, the authenticity can be a unique identification for each individual item, e.g., a barcode.

Figure 3:
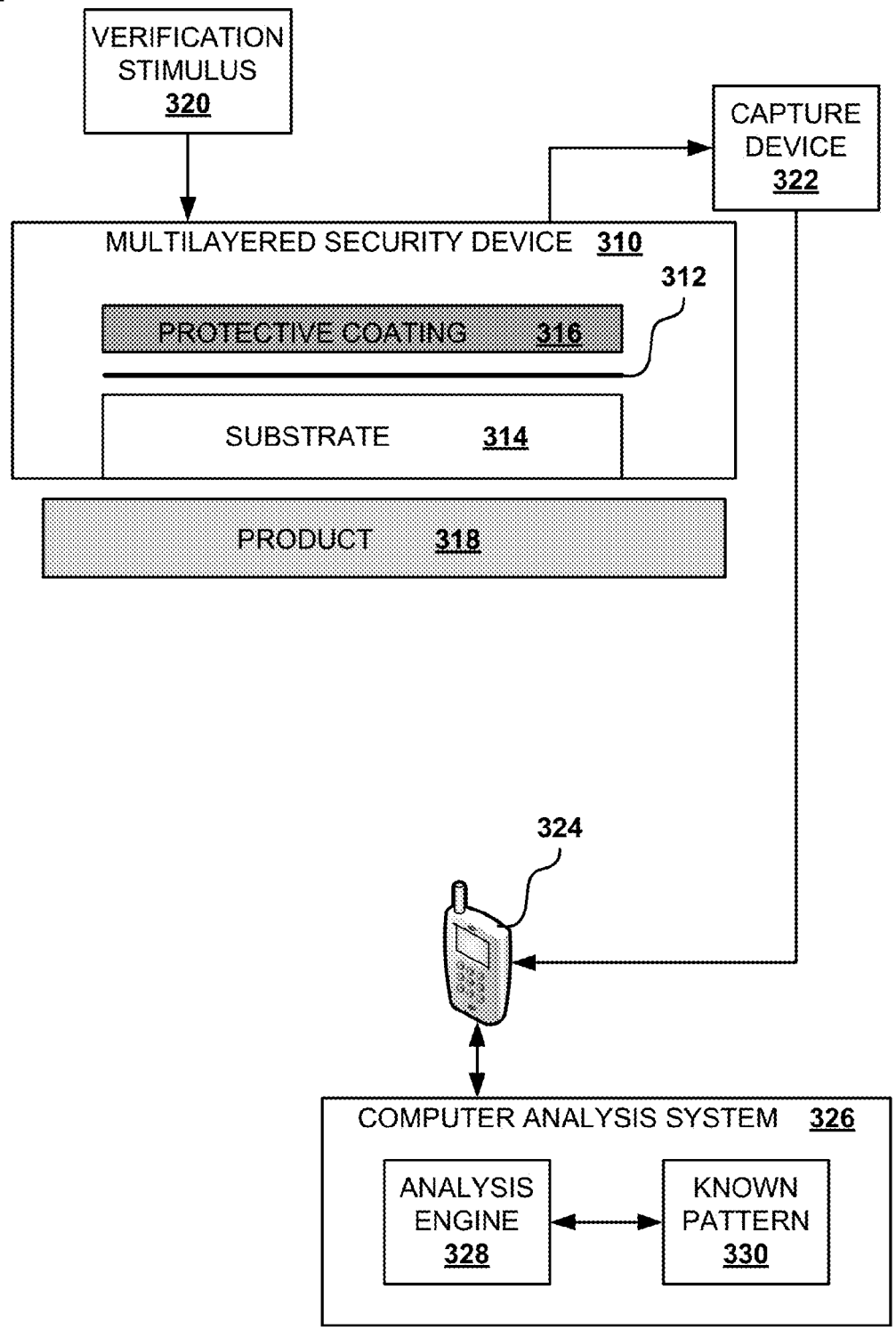
FIG. 3 illustrates a block diagram of a system for verifying the authenticity of a multilayered security device, according to various embodiments.

FIG. 3 illustrates a block diagram of a system 300 for verifying the authenticity of a multilayered security device, according to various embodiments. The system 300 can include a multilayered security device 310, a product 318, a verification stimulus 320, a capture device 322, and a mobile device 324. The system 300 components may work together to verify the authenticity of the product 318.

The multilayered security device 310 is a security device that attaches to the product 318. The multilayered security device 310 can have a graphene layer 312 with up to 10 graphene sheets arranged substantially parallel to one another so that each sheet is visually distinguishable from another sheet. For example, a first graphene sheet forms a first optically contrasting pattern with respect to the substrate and a second optically contrasting pattern with respect to a second graphene sheet. The angle between sheets may depend on the number of layers physically supported by the substrate. The graphene layer 312 will indicate a particular pattern, i.e., a fingerprint, when exposed to a verification stimulus 320, according to various embodiments. The graphene layer 312 can be between a substrate layer 314 and a protecting coating layer 316.

In various embodiments, the multilayered security device 310 is a monolayer of graphene 312 on a 90 nm thick $SiO_2$ layer covering a Si substrate. Various spacing between graphene patterns may include: 0.125 mm, 0.25 mm, 0.5 mm, and 1 mm spacing between patterned graphene strips. The graphene layer may be made of one or more graphene sheets. Each graphene sheet is made of covalently-bonded carbon atoms in a continuous single sheet.

In various embodiments, the combination of multiple layers of graphene 312, variation in alignment of the resist to the template, and oxide thickness variations may lead to a very complex contrasting pattern of each graphene fingerprint which makes the graphene fingerprint very difficult to reproduce. The contrasting pattern is a result of the interaction between a graphene sheet and a substrate when exposed to a verification stimulus, e.g., visible light. An aspect of making the graphene fingerprint unique is the dimension of the pattern itself. For in-field identification, a complex pattern may be resolved with an exposure to a verification stimulus 320 and the capture device 322. In various embodiments, the verification stimulus 320 may be visible light and the capture device 322 may be a digital camera present in cell phones.

The substrate layer 314 may be designed to enhance the contrast with the graphene layer 312. The substrate layer 314 can include various substrates such as $SiO_2$, Si, or PET. The thickness of the substrate layer 314 depends on the degree of contrast required with the graphene layer 312 because of light absorption by the substrate layer. The substrate layer absorbs various light wavelengths due to the type of atoms that constitute the substrate layer. For example, a $SiO_2$ substrate can be 50-100 nm thick or between 250 nm-300 nm thick to show contrast with a monolayer of graphene for 550 nm wavelength light. Increased number of layers of graphene may also increase the contrast. Thus, for a set contrast, increasing the number of graphene layers can allow for a reduction in the thickness of $SiO_2$ substrate.

The substrate layer 314 can also be composed of different substances in different layers, e.g., a base layer of silicon with a top layer of $SiO_2$. In various embodiments, the substrate layer 314 may also be patterned, e.g., regions of $SiO_2$ embedded within a silicon substrate where the surfaces of both materials is coplanar. Combining the graphene layer 312 with a patterned substrate may increase the complexity of the underlying pattern. Complex fingerprints can be created with graphene, particularly when several layers are used. The pattern may be more complex than using only a patterned substrate. The monolayer thickness of the graphene in the graphene layer 312 provides an anti-tampering feature and will be damaged if the adhesive is removed. Graphene patterns can also be much more randomized when patterned graphene is transferred to a patterned substrate at an arbitrary angle.

In various embodiments, the substrate layer 314 may have varying degrees of transparency to enhance visual fingerprints. A highly transparent substrate such as SiC or sapphire may allow for transmitting light through the graphene to determine the contrast as discussed further herein.

The protective coating layer 316 may be configured to allow the graphene layer 312 to be visible when exposed to the light source or otherwise provide minimal interference with either the verification stimulus 320 or capture device 322. The protective coating layer 316 may form a protective barrier around the graphene layer 312 with minimal interference of the contrasting pattern formed between the graphene layer 312 and the substrate. The protective coating layer 316 may be a polymer with a low refractive index.

The verification stimulus 320 may be electromagnetic radiation, according to various embodiments. The electromagnetic radiation may include visible light a particular wavelength or non-visible ultra-violet light, including multiple wavelengths, to the multilayered security device 310. In various embodiments, the verification stimulus 320 may apply visible light so that the visible light is reflected as ambient light to the multilayered security device 310. The reflection or refraction of light can show a pattern within the graphene layer 312. The pattern can be captured by a capture device 322 (e.g., a camera).

The capture device 322 can capture a fingerprint indicating a pattern within the multilayered security device 310. The capture device can depend on the verification stimulus used. For example, if the verification stimulus is a visible light source, then the capture device can be a camera (e.g., cell phone camera). If the verification stimulus is an electrical charge, then the capture device can be a potentiometer to measure resistance or other electrical properties of the graphene. If the verification stimulus is a thermal source (e.g., infrared light), then the capture device can be a thermal imaging camera. The fingerprint can be a visual pattern or an electrostatic pattern. The fingerprint can also be heat based due to the different thermal properties of graphene when compared to an underlying substrate. The capture device 322 has a sufficient resolution to identify the pattern in the multilayered security device 310. For example, if the pattern is visual and very small, then a higher resolution camera may be required to identify the pattern. Likewise, if the pattern is electrostatic, then the capture device 322 has sufficient sensitivity to account for changes in resistance in graphene.

In various embodiments, the capture device 322 captures an image. The resolving capability degrades if the capture angle is high. For example, an incident angle of image capture may reduce the resolution compared to a direct image capture. The angle to take the image may be significant, and image recognition software (i.e., the analysis engine 328) is needed for authentication. The capture device 322 can transmit the signature to a mobile device 324.

The mobile device 324 can host the computer analysis system 326. In various embodiments, the computer analysis system 326 is cloud-based and a node of the cloud computing system is the mobile device 324. The computer analysis system 326 can analyze the captured pattern and compare the captured pattern with an expected pattern 330. The computer analysis system 326 can have a library of one or more expected patterns 330 and an analysis engine 328. The analysis engine 328 may perform the analysis of captured patterns to determine if there is a match with an expected pattern. In various embodiments, the analysis engine 328 can label the product as authentic in response to the captured pattern matching the expected pattern. The captured pattern may be a match with the expected pattern if the verification stimulus, when applied to the multilayered security device, causes the multilayered security device to produce the expected pattern. For example, if the verification stimulus is an electrical charge, then the captured pattern would reveal a variety of electrical properties within the multilayered security device in a three-dimensional space. The captured pattern can be compared to the expected pattern within the three-dimensional space of the multilayered security device.

Figure 4B:
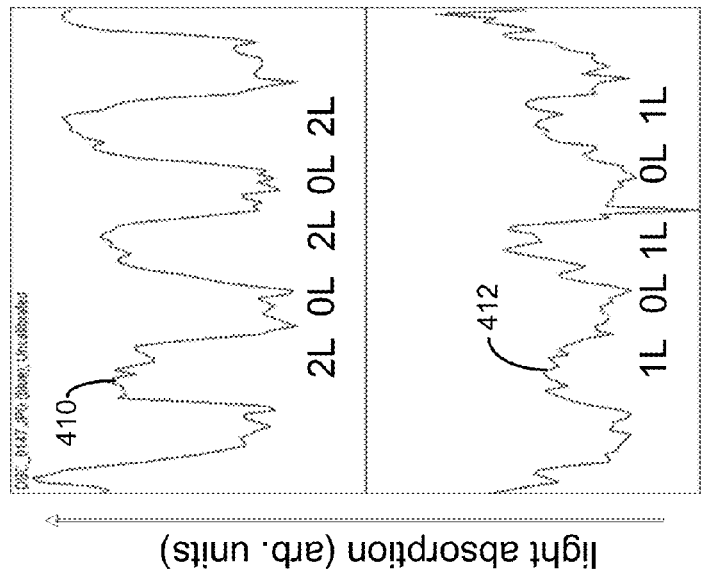
FIG. 4B illustrates two plots of the contrast between one layer and two layers of graphene, according to various embodiments.
Figure 4A:
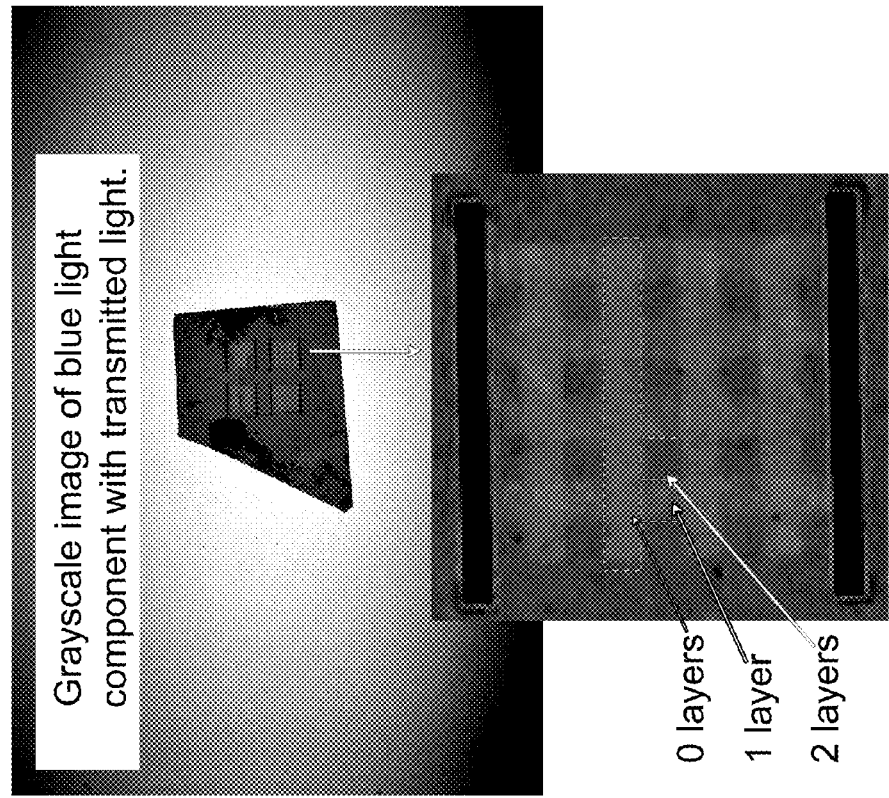
FIG. 4A illustrates an image of a multilayered security device with light absorption, according to various embodiments.

FIG. 4A illustrates an image of a multilayered security device with light absorption, according to various embodiments. The image may illustrate transmitted light through the multilayered security device. The multilayered security device may have interlocking strips of graphene on a SiC substrate. Multiple layers of graphene are shown. For example, zero layers of graphene show the base SiC substrate as a lighter image than the single graphene layer. The two layer of graphene occurs when two single graphene layers overlap. The contrasting signature may be difficult to reproduce by conventional means.

FIG. 4B illustrates two plots of the contrast between one layer and two layers of graphene, according to various embodiments. The plot 412 illustrating the absorption of light of a single graphene layer versus no graphene layers. The plot 410 illustrating the absorption of light of two graphene layers versus no graphene layers. The light absorption is greater, i.e. contrast is greater, for two graphene layer. Different numbers of graphene layers produce different amounts of light transmission through the patterned multilayered security device. This step like light absorption characteristic of graphene can be utilized in the multilayered security device pattern.

Figure 5:
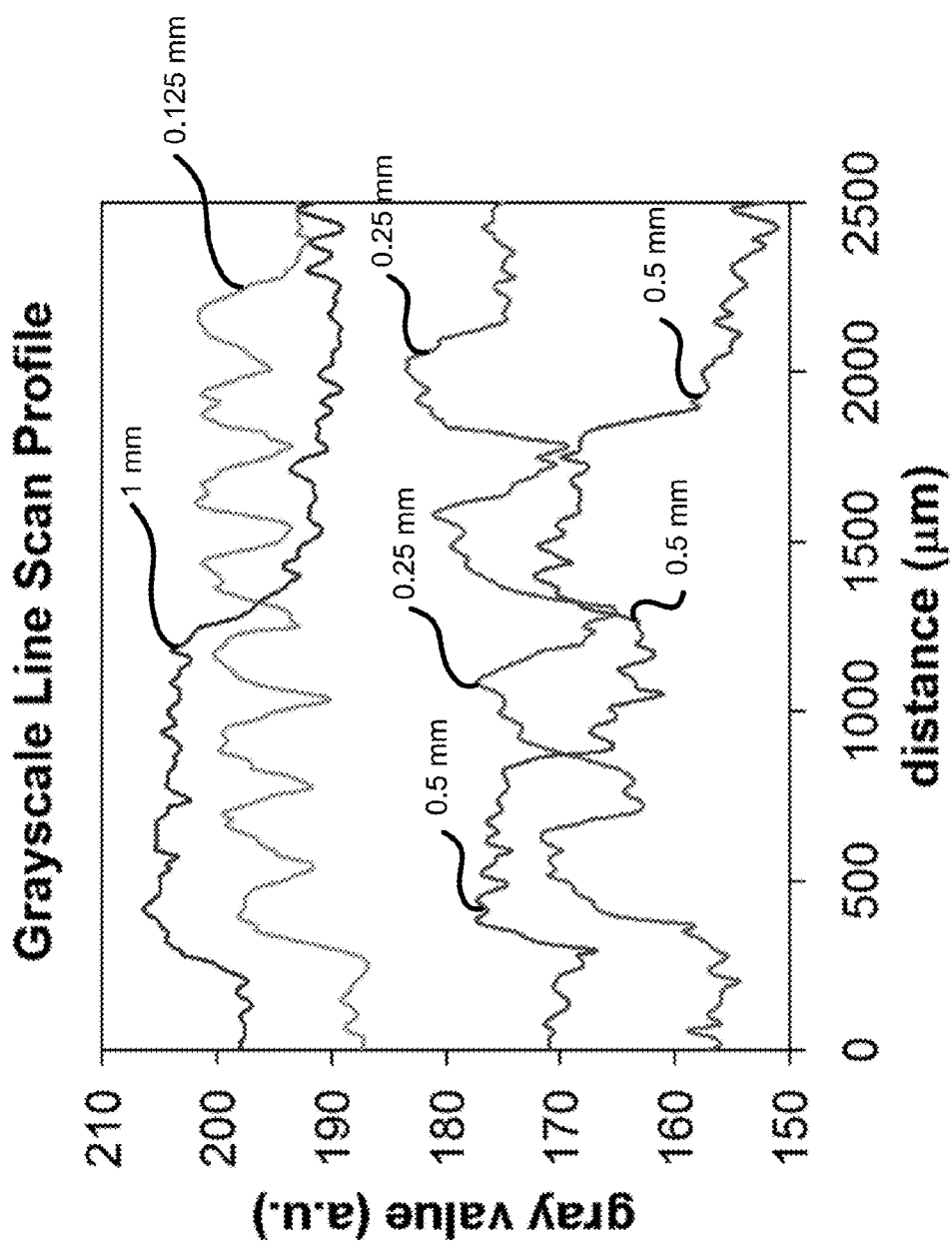
FIG. 5 illustrates an absorption graph of graphene for different pattern spacing in a multilayered security device, according to various embodiments.

FIG. 5 illustrates an absorption graph of graphene for different pattern spacing in a multilayered security device, according to various embodiments. The graph illustrates graphene with 0.125 mm, 0.25 mm, 0.5 mm, and 1 mm spacing. In various embodiments, a computer analysis system can prepare an absorption graph in order to distinguish patterns. The pattern spacing may be limited by the resolution of the capture device. For example, a 10 MegaPixel resolution camera may have noise levels that make it difficult to detect spacing smaller than 0.125 mm.

Figure 6:
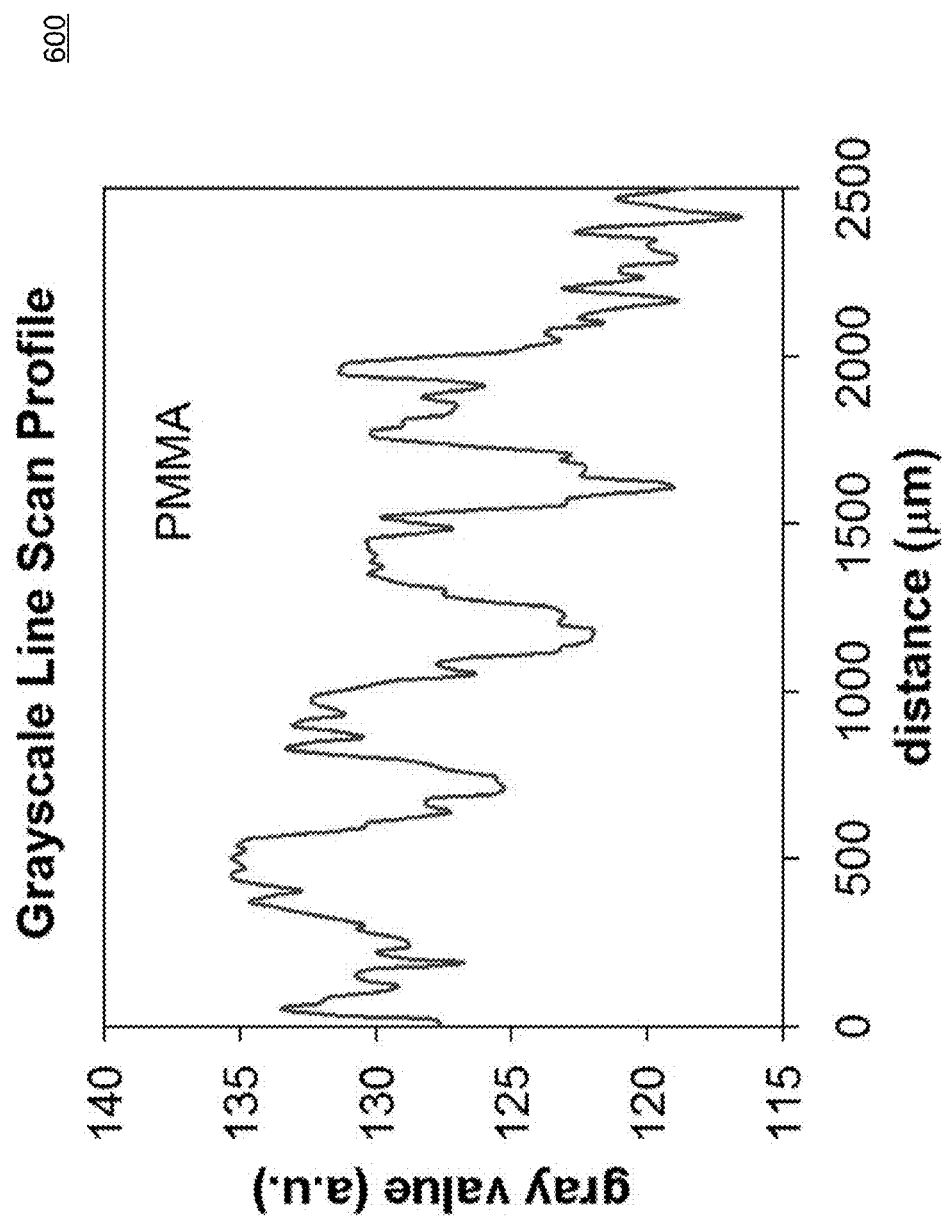
FIG. 6 illustrates an absorption graph of graphene for a 0.25 mm pattern spacing with 140 nm coating of PMMA, according to various embodiments.

FIG. 6 illustrates an absorption graph 600 of graphene for a 0.25 mm pattern spacing with 140 nm coating of PMMA, according to various embodiments. The absorption graph 600 illustrates the absorption of light by the graphene. The spacing and resolution of the graphene pattern remains intact.

Figure 7B:
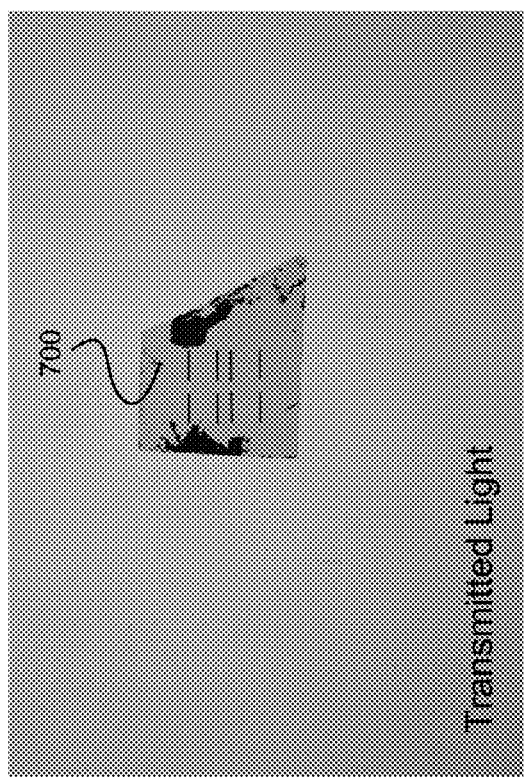
FIG. 7B illustrates an image of a multilayered security device using a transparent substrate and transmitted light, according to various embodiments.
Figure 7A:
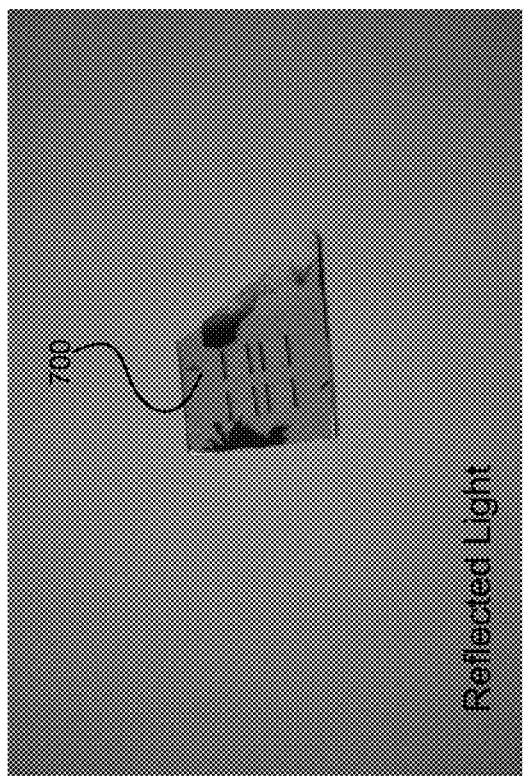
FIG. 7A illustrates an image of a multilayered security device using a transparent substrate and reflected light, according to various embodiments.

FIG. 7A illustrates an image of a multilayered security device 700 using a transparent substrate and reflected light, according to various embodiments. The multilayered security device 700 may have a PMMA substrate overlaid with a graphene layer. The reflected light may be light that is reflected from the substrate and may provide enhanced resolution in certain circumstances. For example, the product may not be sufficiently transparent which would block resolution from bottom source light.

FIG. 7B illustrates an image of a multilayered security device 700 using a transparent substrate and transmitted light, according to various embodiments. The transmitted light may be transmitted through the substrate whereas the reflected light is reflected from the substrate. The light transmitted through the substrate may help enhance contrast in low lighting situations.

Figure 8:
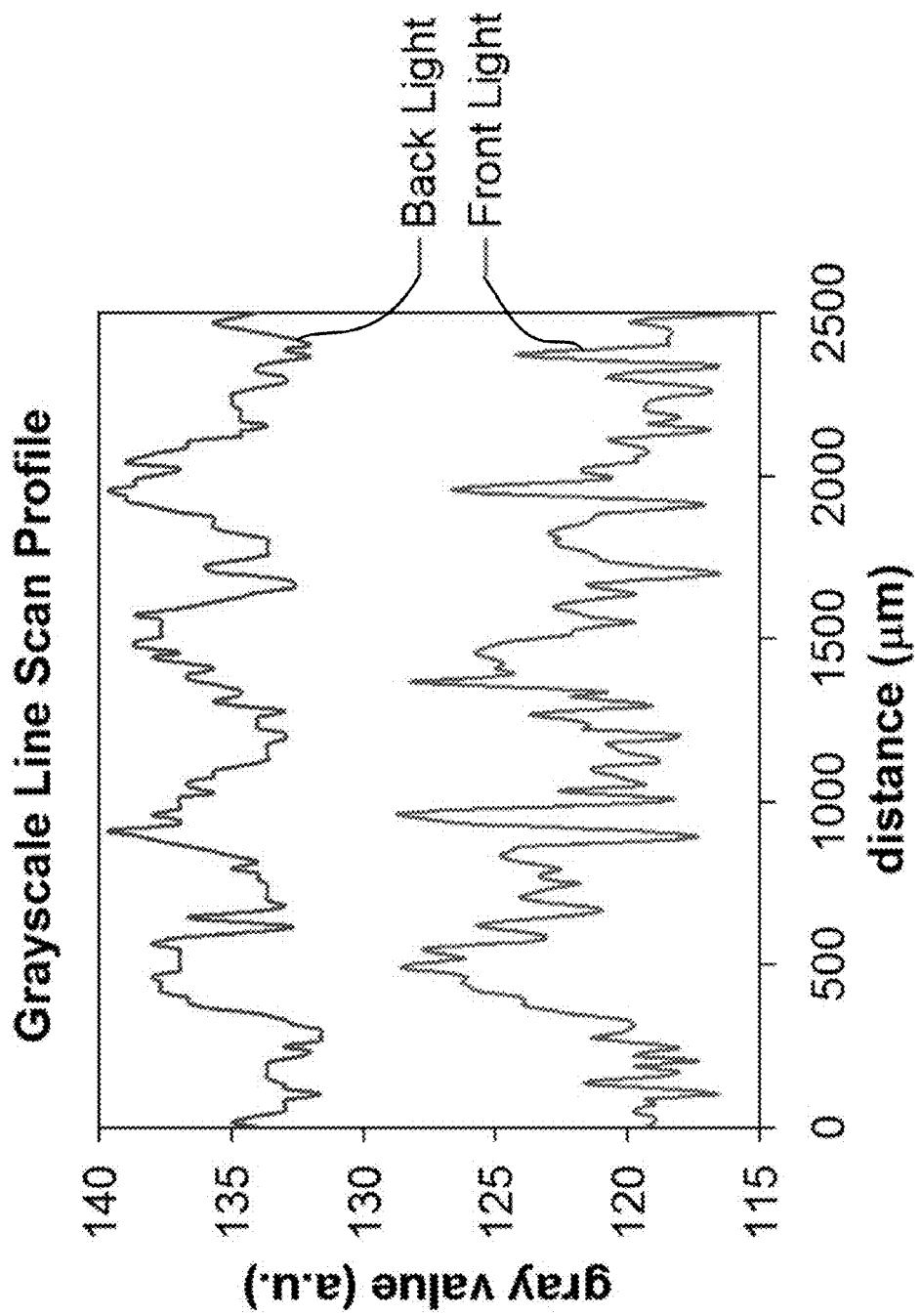
FIG. 8 illustrates an absorption graph for a front lighting and a back lighting of a multilayered security device using a transparent substrate, according to various embodiments.

FIG. 8 illustrates an absorption graph for a front lighting and a back lighting of a multilayered security device using a transparent substrate, according to various embodiments. The front light can correspond to the reflected light in FIG. 7A and the back light can correspond to the transmitted light in FIG. 7B. The absorption and resolution is higher for the transmitted light.

Figures 9A, 9B:
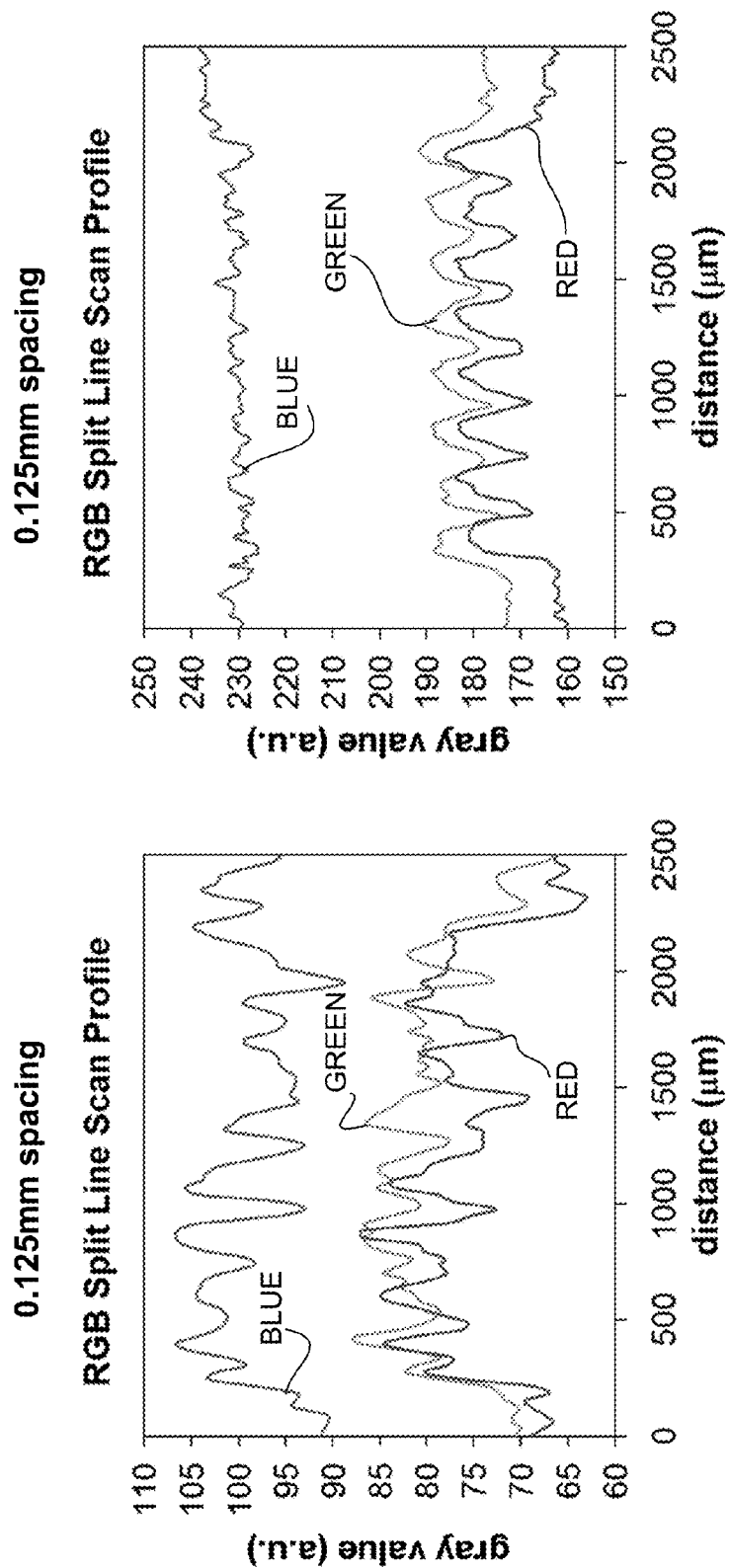
FIG. 9A illustrates an absorption graph with 1 MP resolution for 0.125 mm spacing of graphene on a multilayered security device, according to various embodiments.
FIG. 9B illustrates an absorption graph with 10 MP resolution for 0.125 mm spacing of graphene on a multilayered security device, according to various embodiments.

FIG. 9A illustrates an absorption graph with 1 MP resolution for 0.125 mm spacing of graphene on a multilayered security device, according to various embodiments. The absorption graph illustrates the various wavelengths of light that are better absorbed by the graphene and the resolution of the peaks. The 1 MP resolution may not be sufficient to distinguish the line spacing between graphene strips for any wavelength of light due to the noise.

FIG. 9B illustrates an absorption graph with 10 MP resolution for 0.125 mm spacing of graphene on a multilayered security device, according to various embodiments. The 10 MP of light appears to have higher resolution sufficient to distinguish graphene spacing for green and red wavelengths of light. At 10 megapixels (MP), a RGB line scan profile is identified for graphene barcode line widths of just 125 µm. Several of the most popular cell phone options have near 10 MP or greater, indicating the possibility to read these scaled graphene patterns. In various embodiments, complex patterns are recognizable even with a low-resolution camera if the graphene pattern feature sizes are within a certain size. These scaled complex patterns may be small which would allow the barcode itself to be very small. A small complex pattern may be disadvantageous in products where it is desirable or common to use the graphene pattern for low-resolution capture devices. Pattern size and contrast are determined with regard to a complex pattern which can still be resolved by inexpensive cameras. Pattern complexity and resolution are correlated to various imaging techniques ranging from optical microscopes, digital cameras, scanning electron microscopes (SEM) and other imaging techniques to produce a cost effective identification procedure.

Figure 10A:
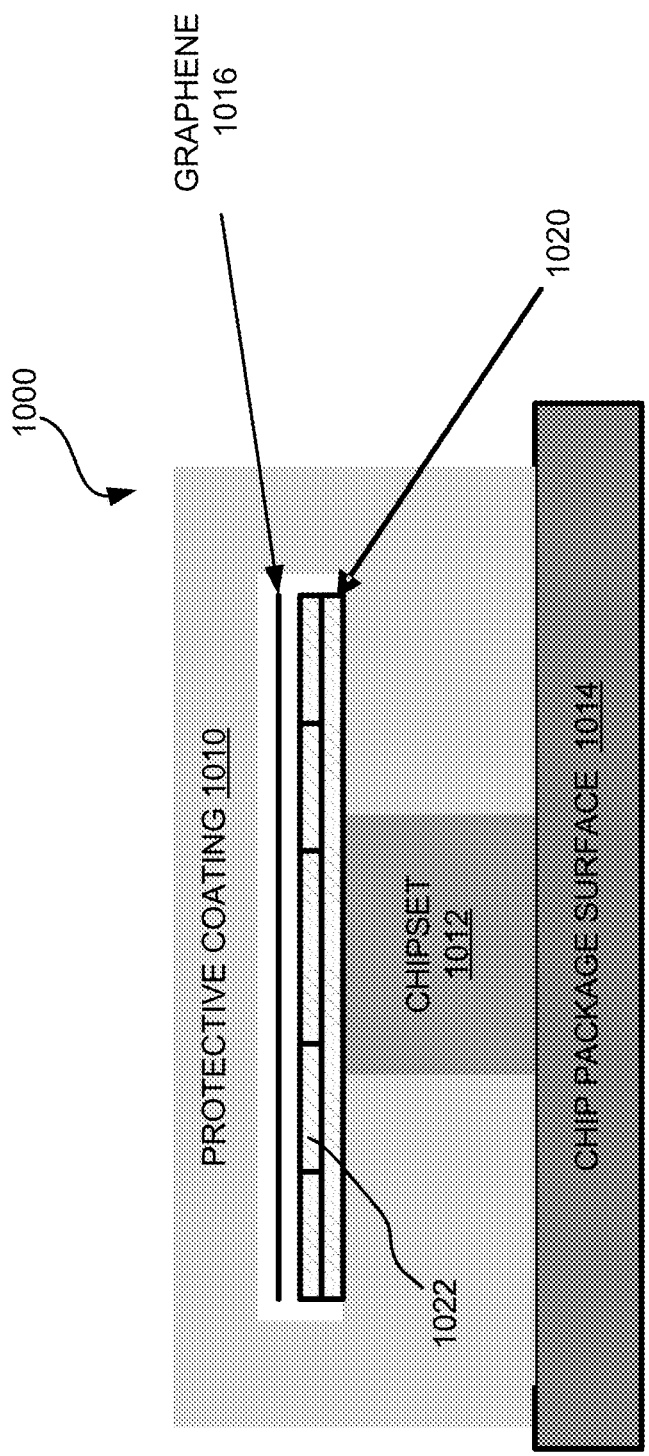
FIG. 10A illustrates a side-view of a multilayered security device applied to a chipset product, according to various embodiments.

FIG. 10A illustrates a side-view of a multilayered security device 1000 applied to a chipset product, according to various embodiments. The multilayered security device 1000 can verify the authenticity of a chipset product 1012. The chipset 1012 may be attached to the chip packaging surface 1014 with the protective coating layer 1010.

The protective coating layer 1010 is a layer that serves as a protective barrier for the graphene layer 1016. In various embodiments, the protective coating layer 1010 can be extended around the multilayered security device 1010 to be used as an adhesive for the substrate layer 1020 to the product. The protective coating layer 1010 can be made of PMMA. The substrate layer 1020 can be formed from silicon with $SiO_2$-filled wells 1022 fabricated coplanar with the silicon surface to enhance the contrast of graphene, making it visible in these regions.

In various embodiments, the chipset 1012 may also be a chiplet. The multilayered security device 1000 can protect the chiplet attached externally to a fully packaged chip against removal or tampering. The graphene layer 1016 may contain a unique fingerprint to cover the chiplet. The fingerprint can be imaged and identified optically using common imaging methods such as (cell phone) digital cameras or optical microscopes and is unclonable due to the unique pattern within the graphene and its optical properties. Since graphene is fragile, removal of chiplet attached to integrated circuit component would be nearly impossible without destroying the graphene layer 1016. The code obtained from the unique fingerprint pattern in the graphene can be linked to the authentication code of the chiplet in order to ensure each chiplet has its own unique graphene patch. If the patch is removed or broken, the fingerprint may not be reconstructed and therefore the chiplet has been compromised. The graphene layer 1016 can have a plurality of graphene sheets and be in a single plane or in multiple planes. In various embodiments, a graphene sheet may intersect with another graphene sheet at a particular angle of incidence.

In various embodiments, the fabrication of the multilayered security device 1000 can utilized operations 118 and operation 120 from FIG. 1. For example, graphene may be transferred onto a patterned silicon/silicon oxide surface. The graphene fingerprint is fabricated by patterning the resist using photolithography. After resist development, the exposed graphene will be removed by ashing followed by removal of the resist using a solvent strip. After pattern generation the wafer will be thinned and diced so that the graphene multilayered security device containing the patterned substrate and the patterned graphene is flexible. The patch is transferred to the chiplet and the graphene multilayered security device with the fingerprint will be covered with crosslinked glue (polymer) to attach the chiplet to the fully packaged chip. The fingerprint within the graphene will be imaged and then via image analysis be authenticated. Since the code from the fingerprint is linked to the code of the chiplet, any destruction for the graphene will show that the chiplet is compromised.

Figure 10B:
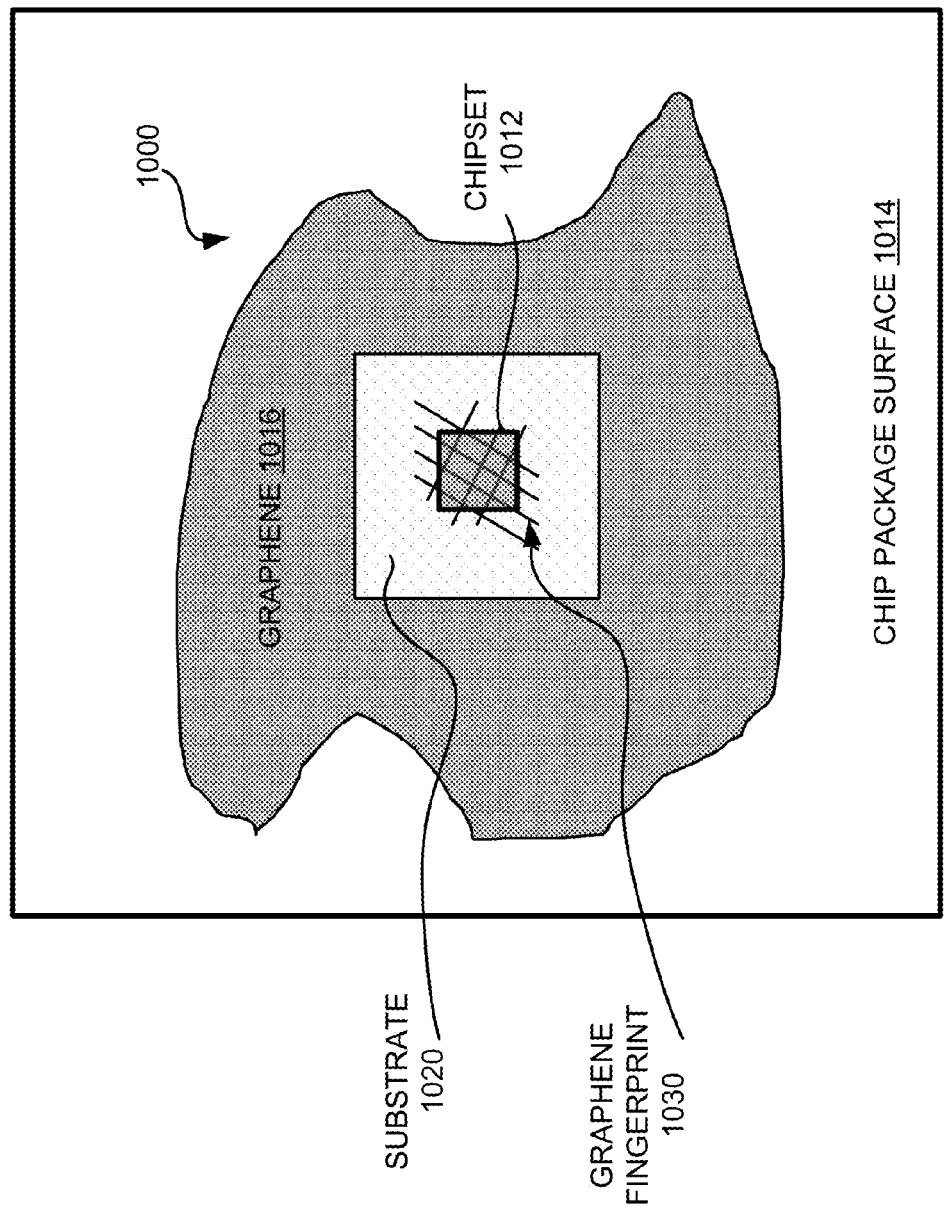
FIG. 10B illustrates a top-view of a multilayered security device applied to a chipset product, according to various embodiments.

FIG. 10B illustrates a top-view of a multilayered security device 1000 applied to a chipset product, according to various embodiments. The top-view of the multilayered security device 1000 may have the same components shown in the side-view. The graphene 1016 may be formed from a single monolayer and in a non-standard shape that covers the substrate 1020 entirely. The graphene 1016 may overlap with $SiO_2$ wells (not shown) and create the graphene fingerprint 1030.

Figure 11A:
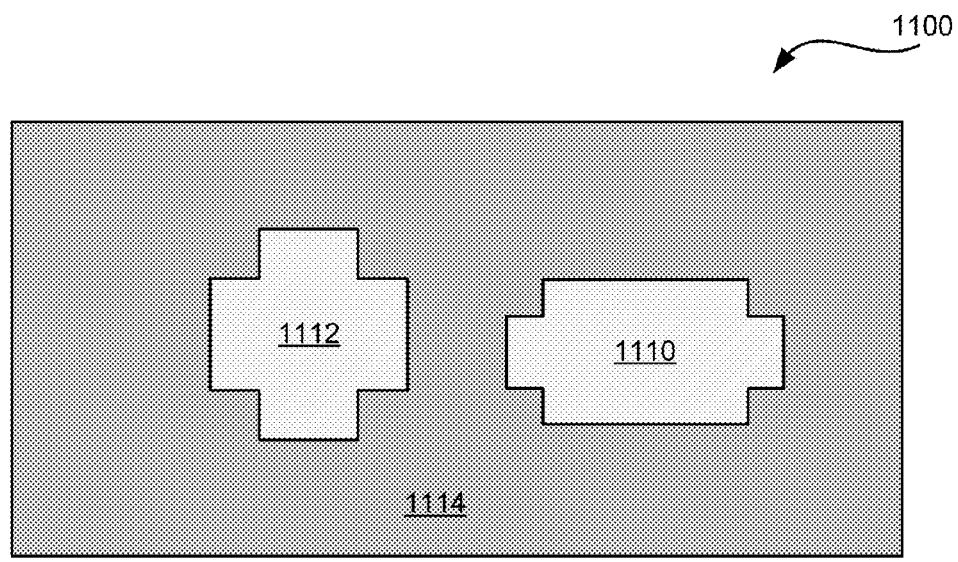
FIG. 11A illustrates a top-view of a substrate layer of a multilayered security device 1200, according to various embodiments.

FIG. 11A illustrates a top-view of a substrate layer 1114 of a multilayered security device 1100, according to various embodiments. The substrate layer 1114 can be silicon. Various wells, 1110 and 1112 can be made out of $SiO_2$. The wells 1110, 1112 can be created using various forms. In various embodiments, the wells are not patterned or shaped and are random in formation. The wells 1110, 1112 may not have uniform thickness. For example, well 1110 may have a thickness of 90 nm while well 1112 may have a thickness of 300 nm.

Figure 11B:
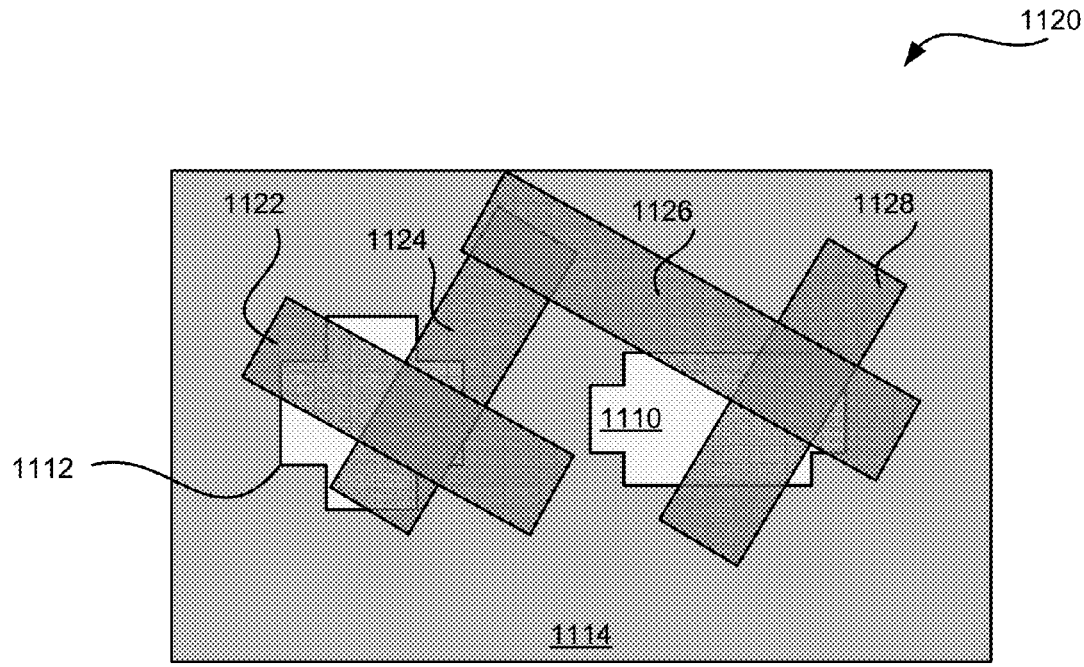
FIG. 11B illustrates a top-view a multilayered security device, according to various embodiments.

FIG. 11B illustrates a top-view a multilayered security device 1120, according to various embodiments. The multilayered security device 1120 can have the wells 1110, 1112 on the substrate 1114 like the multilayered security device 1100. In addition, graphene sheets 1122, 1124, 1126, and 1128 can be transferred to the substrate 1114. The graphene sheets can be transferred in any predetermined pattern. For example, the graphene sheets can form two layers on top of the substrate 1114 and wells 1110, 1112. For example, graphene sheet 1124 and graphene sheet 1128 can be transferred first and reside in graphene layer one. Graphene sheet 1122 and graphene sheet 1126 can reside in graphene layer two. Intersecting regions can form on top of graphene sheet 1124 and graphene sheet 1128.

In various embodiments, the graphene sheets may be on different planes. The graphene sheet 1124 and graphene sheet 1128 can occupy a first plane. The graphene sheet 1122 and graphene sheet 1126 can occupy a second plane. In various embodiments, graphene sheets may occupy two or more planes. For example, if a first graphene sheet is in a first plane and a second graphene sheet is in a second plane that is substantially parallel to the first plane, then there may be a third graphene sheet that intersects the first graphene sheet and second graphene sheet at a particular angle of incidence (e.g., not perpendicular and at an incident angle to either the first or second graphene sheet).

Figure 11C:
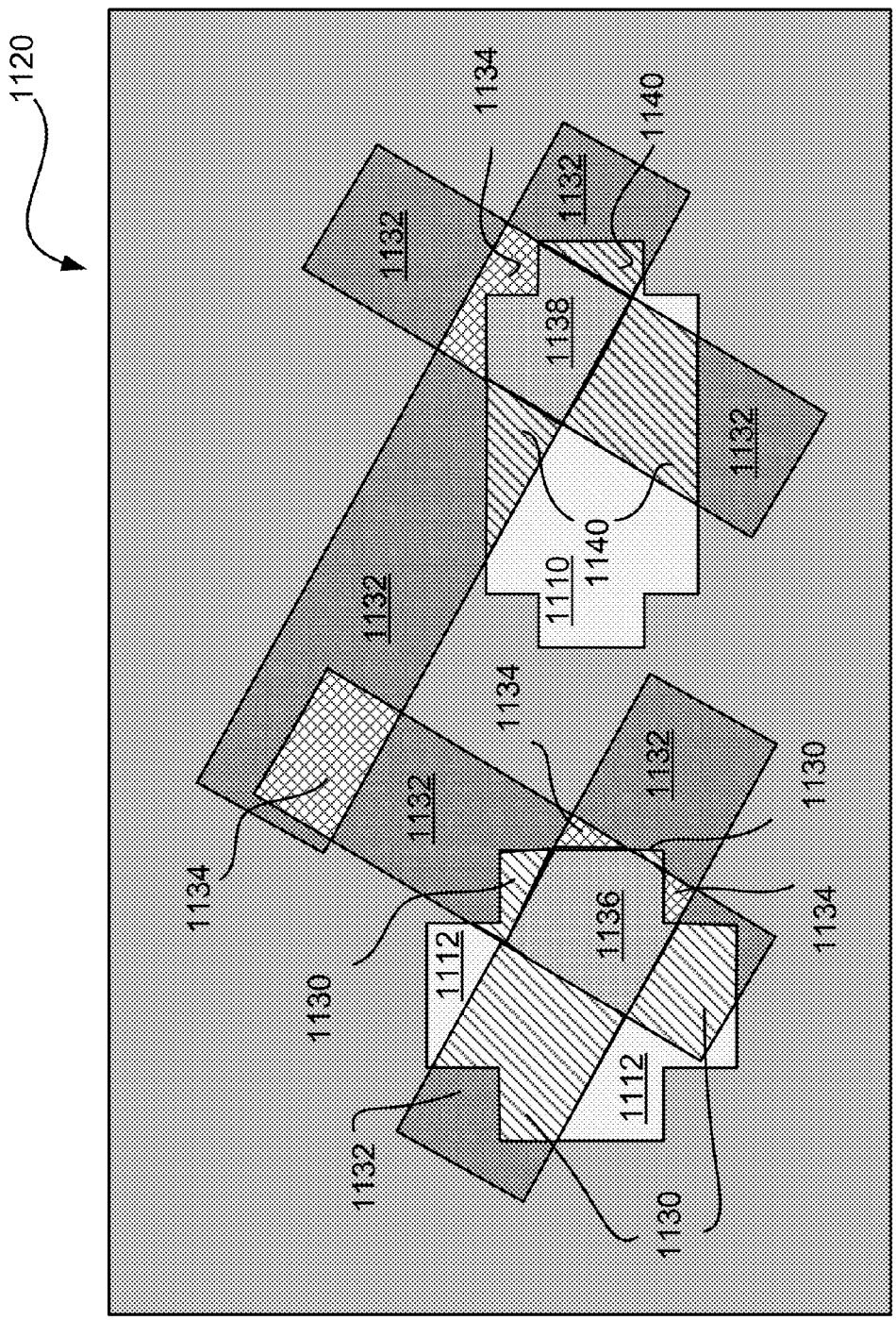
FIG. 11C illustrates a top-view of the multilayered security device, according to various embodiments.

FIG. 11C illustrates a top-view of the multilayered security device 1120, according to various embodiments. The graphene sheets described in FIG. 11B create areas of different optical properties. For example, each addition graphene sheet, when layered, absorbs about 3% of the light and creates a complicated three dimensional image for a flat surface. In multilayered security device 1120, the wells may be of different thickness. Thus, a number of different areas are created. The regions are described in terms of low-contrast to high-contrast. A low-contrast area 1132 is the silicon substrate against graphene sheets. Another low-contrast area 1134 is formed by the intersection of two different graphene layers against a silicon substrate. A high contrast area 1130 is created by the monolayer of graphene against the 300 nm thick $SiO_2$ well 1112. A different high contrast area 1140 is formed by a single monolayer of graphene against the 90 nm thick $SiO_2$ well 1110. The highest contrast areas are formed with two monolayers of graphene sheets and the $SiO_2$ wells. For example, area 1136 is formed from the intersection of two graphene sheets and the 300 nm $SiO_2$ substrate 1112. Area 1138 is formed from the intersection of two graphene sheets and the 90 nm $SiO_2$ substrate 1110. A computer analysis system can detect the varying levels of contrast, i.e., the pattern, within the multilayered security device 1120 and compare against an expected pattern to verify a product.

In various embodiments, the wells 1110, 1112 may be exposed relative to the graphene sheets 1122, 1124, 1126, and 1128. The wells 1110, 1112 and the substrate 1114 form an exposed substrate area. The exposed substrate area may have multiple contrasting images. For example, the well 1112 not covered by the graphene sheet 1122 and 1124 may be a first contrasting pattern while the substrate that is not covered by the graphene sheets 1122,1124 may be a second contrasting pattern. For example, area 1130 formed between the well 1112 and graphene sheets 1122, 1124 are a different contrasting pattern than area 1132 which is formed between the substrate 1114 and a single graphene sheet, e.g., 1122, 1124, 1126, and 1128.

In various embodiments, an exposed substrate area is not the only structure to produce a contrasting pattern. An underlying substrate area may also produce a contrasting pattern. Multiple layers of graphene sheets may form different contrasting patterns within the graphene sheet. For example, the area 1136 formed between two graphene sheets 1124 and 1122 with the well 1112 is optically distinct from the contrasting pattern from area 1134 formed between the two graphene sheets 1124 and 1122 with the substrate 1114. The contrasting pattern produced from area 1134 may also be different than area 1132 due to the intersection of 1124 and 1126, despite the same substrate 1114 underlying both areas 1132, 1134.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:

1. A method of verifying a product using a multilayered security device, comprising:
   applying, by an antenna of a capture device, a low-power radio frequency (RF) signal to a security device attached to the product,
   wherein the security device includes an Organic Light Emitting Diode (OLED) substrate with an embedded RF coil, the embedded RF coil causing the OLED substrate to emit light in response to the applied low-power RF signal, the security device further comprising a graphene sheet made of a monolayer of covalently bonded carbon atoms, the graphene sheet preventing light emitted from the OLED substrate to form a contrasting pattern of emitted light;
   receiving, by a camera of the capture device and in response to the applied low-power RF signal, a captured pattern from the contrasting pattern of emitted light of the security device
   determining the captured pattern matches an expected pattern; and
   verifying the authenticity of the product in response to the captured pattern matching the expected pattern.

2. The method of claim 1, wherein the capture device is a cellphone.

3. The method of claim 1, wherein the security device further comprises a second graphene sheet made of a monolayer of covalently bonded carbon atoms, and wherein the contrasting pattern of emitted light is also formed from the second graphene sheet.

4. The method of claim 1, wherein the security device further comprises a protective coating layer over the OLED substrate and the graphene sheet.

5. The method of claim 4, wherein the protective coating is a polymer with a low refractive index.

6. The method of claim 4, wherein the protective coating is configured to enhance contrast of the graphene layer.

7. The method of claim 1, wherein the OLED substrate of the security device may be patterned with an embedded silicon dioxide material to increase the complexity of the contrasting pattern of emitted light.

8. The method of claim 1, wherein the expected pattern is stored on the cellphone, and wherein the determining the captured pattern matches an expected pattern is comparing by the cellphone.

9. The method of claim 1, wherein the expected pattern is stored on a node of a cloud computing system, and wherein the determining the captured pattern matches an expected pattern is performed by the node.

* * * * *